(12) United States Patent
Shen et al.

(10) Patent No.: US 10,748,069 B2
(45) Date of Patent: Aug. 18, 2020

(54) METHOD AND APPARATUS FOR PERFORMING BLOCK RETRIEVAL ON BLOCK TO BE PROCESSED OF URINE SEDIMENT IMAGE

(71) Applicant: Siemens Healthcare Diagnostics Inc., Tarrytown, NY (US)

(72) Inventors: Tian Shen, Xi An (CN); Juan Xu, Beijing (CN); XiaoFan Zhang, Charlotte, NC (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 866 days.

(21) Appl. No.: 15/306,897

(22) PCT Filed: Apr. 30, 2015

(86) PCT No.: PCT/US2015/028441
§ 371 (c)(1),
(2) Date: Oct. 26, 2016

(87) PCT Pub. No.: WO2015/168366
PCT Pub. Date: Nov. 5, 2015

(65) Prior Publication Data
US 2017/0046621 A1    Feb. 16, 2017

(30) Foreign Application Priority Data
Apr. 30, 2014    (CN) .......................... 2014 1 0183615

(51) Int. Cl.
*G06N 5/04*    (2006.01)
*G06N 20/00*    (2019.01)
(Continued)

(52) U.S. Cl.
CPC ............ *G06N 5/045* (2013.01); *G01N 33/493* (2013.01); *G06F 16/9027* (2019.01); *G06K 9/6282* (2013.01); *G06N 20/00* (2019.01)

(58) Field of Classification Search
None
See application file for complete search history.

(56) References Cited

U.S. PATENT DOCUMENTS 5,911,002 A * 6/1999 Mitsuyama .......... G01N 33/493
                                                            382/156
6,047,283 A * 4/2000 Braun .................... G06F 16/322
(Continued)

FOREIGN PATENT DOCUMENTS

CN    102629376 A    8/2012
CN    103093453 A    5/2013
(Continued)

OTHER PUBLICATIONS

Almadhoun et al, Automated recognition of urinary microscopic solid particles, 2013 Informa UK Ltd. DOI: 10.3109/03091902.2013.863394 (Year: 2013).*
(Continued)

*Primary Examiner* — Andrae S Allison
(74) *Attorney, Agent, or Firm* — Dunlap Codding P.C.

(57) ABSTRACT

The inventive concepts herein relate to performing block retrieval on a block to be processed of a urine sediment image. The method comprises: using a plurality of decision trees to perform block retrieval on the block to be processed, wherein each of the plurality of decision trees comprises a judgment node and a leaf node, and the judgment node judges the block to be processed to make it reach the leaf node by using a block retrieval feature in a block retrieval feature set to form a block retrieval result at the leaf node, and at least two decision trees in the plurality of decision trees are different in structures thereof and/or judgments
(Continued)

performed by the judgment nodes thereof by using the block retrieval feature; and integrating the block retrieval results of the plurality of decision trees so as to form a final block retrieval result.

12 Claims, 3 Drawing Sheets

(51) Int. Cl.
*G06F 16/901* (2019.01)
*G01N 33/493* (2006.01)
*G06K 9/62* (2006.01)

(56) References Cited

U.S. PATENT DOCUMENTS

| | | | | |
|---|---|---|---|---|
| 6,246,785 | B1* | 6/2001 | Molnar | G01N 15/1475 382/133 |
| 6,704,719 | B1 | 3/2004 | Ericson | |
| 8,533,129 | B2* | 9/2013 | Kejariwal | G06N 20/00 706/12 |
| 9,229,956 | B2* | 1/2016 | Ke | G06F 16/532 |
| 2005/0225678 | A1* | 10/2005 | Zisserman | G06K 9/00208 348/571 |
| 2008/0104102 | A1* | 5/2008 | Zhang | G06F 16/2272 |
| 2010/0226564 | A1* | 9/2010 | Marchesotti | G06K 9/4671 382/159 |
| 2010/0260401 | A1* | 10/2010 | Spitzer | G06T 5/008 382/131 |
| 2011/0076685 | A1 | 3/2011 | Moeller et al. | |

FOREIGN PATENT DOCUMENTS

| | | |
|---|---|---|
| CN | 103392183 A | 11/2013 |
| EP | 0644414 A2 | 3/1995 |
| WO | 2012015904 A2 | 2/2012 |
| WO | 2014012176 A1 | 1/2014 |

OTHER PUBLICATIONS

Li et al, Decision tree and bagging algorithm for the automatic identification of epithelial cell of wound, IOP Conf. Series: Journal of Physics: Conf. Series 1087 (2018) 022014 (Year: 2018).*

Lee, JS-J., et al. "Integration of neural networks and decision tree classifiers for automated cytology screening." IJCNN-91—Seattle International Joint Conference on Neural Networks. vol. 1. IEEE, 1991. (Year: 1991).*

International Search Report and Written Opinion of International Application No. PCT/US2015/028441 dated Aug. 7, 2015.

Breiman,"Random Forests", 2001, Machine Learning, 45, pp. 5-32.

Sivic et al.,"Video Google: A Text Retrieval Approach to Object Matching in Videos", Proceedings of the Ninth IEEE International Conference on Computer Vision (ICCV 2003) 2-Volume Set, pp. 1-8.

Nister et al.,"Scalable Recognition with a Vocabulary Tree", Proceedings of the 2006 IEEE Computer Society Conference on Computer Vision and Pattern Recognition (CVPR'06), pp. 1-8.

Jegou et al.,"Hamming embedding and weak geometric consistency for large scale image search", ECCV 2008—10th European Conference on Computer Vision, Oct. 2008, Marseille, France, pp. 1-16.

European Office Action of European Application No. 15786785.4 dated Mar. 27, 2019.

European Search Report and Written Opinion of European Application No. 15786785.4 dated Apr. 19, 2017.

Melder et al.,"Automated Image Analysis in the Diagnosis of Bladder Cancer"; Aug. 15, 1987, Applied Optics, vol. 26, No. 16, p. 3367-372.

Abellán et al., "Bagging Decision Trees an Data Sets with Classification Noise", Feb. 2010, Springer International Publishing, Network and Parallel Computing, pp. 248-265.

Wu et al., "An Adaptive Sampling Ensemble Learning Method for Urinalysis Model", Dec. 2010, 2nd International Conference on Information Engineering and Computer Science (ICIECS), pp. 1-4.

* cited by examiner

METHOD AND APPARATUS FOR PERFORMING BLOCK RETRIEVAL ON BLOCK TO BE PROCESSED OF URINE SEDIMENT IMAGE

The subject application claims benefit under 35 USC §119(e) of Chinese Patent Application No. 201410183615.2, filed Apr. 30, 2014. The entire contents of the above-referenced patent application are hereby expressly incorporated herein by reference.

TECHNICAL FIELD

The present invention relates to biological detection, and in particular to a method and apparatus for performing block retrieval on a block to be processed of a urine sediment image.

BACKGROUND ART

In common urine sediment analysis, first, a urine sample image is shot using a microscope system. Then, the candidate blocks in the urine sample image are segmented using, for example, an edge detection technology. By removing obvious background blocks from these candidate blocks, blocks to be processed are detected. Next, the blocks to be processed are processed.

Currently, there are mainly two directions of processing the blocks to be processed. The first direction is classification, i.e. directly classifying these blocks to be processed into various visible element (such as a tubular, an epithelium and an erythrocyte) blocks and background blocks that are easy to be confused with visible elements. The other direction is block retrieval, which does not directly classify the blocks to be processed but retrieves blocks similar to the previously stored blocks to be processed in a database. The unique difference with regard to the result of classification lies in that block retrieval may retrieve a plurality of similar blocks to be provided to a user, and thus can provide more information for the user. The user may perform a further selection or judgment in the plurality of similar blocks.

The block retrieval methods proposed in the prior art have, for example, a feature vector minimum distance method. It is assumed that there are n block retrieval features in a block retrieval feature set. With regard to a specific block, n block retrieval features thereof form an n-dimensional block retrieval feature vector. The distance between the n-dimensional block retrieval feature vector of a block to be processed and an n-dimensional block retrieval feature vector of each stored block is calculated, for example, a Euclidean distance. Then, various stored blocks are arranged successively in an ascending order according to the Euclidean distances of the blocks to be processed and are taken as block retrieval results. In this method, since a large number of blocks are stored in a memory (otherwise, there is no sense to retrieve), a large amount of calculation needs to be done so as to calculate the Euclidean distances between the blocks and the blocks to be processed one by one.

CONTENTS OF THE INVENTION

One embodiment of the present invention aims to improve the efficiency of performing block retrieval on a block to be processed of a urine sediment image.

According to one embodiment of the present invention, a method for performing block retrieval on a block to be processed of a urine sediment image is provided, comprising: using a plurality of decision trees to perform block retrieval on the block to be processed, wherein each of the plurality of decision trees comprises a judgment node and a leaf node, and the judgment node judges the block to be processed to make it reach the leaf node by using a block retrieval feature in a block retrieval feature set to form a block retrieval result at the leaf node, wherein the block retrieval result comprises a retrieved block, and at least two decision trees in the plurality of decision trees are different in structures thereof and/or judgments performed by the judgment nodes thereof by using the block retrieval feature; and integrating the block retrieval results of the plurality of decision trees so as to form a final block retrieval result.

In a particular implementation, the step of integrating the block retrieval results of the plurality of decision trees comprises: voting for the blocks retrieved by the plurality of decision trees, wherein if there are m decision trees in the plurality of decision trees altogether which retrieve a specific block, the ballot of the specific block is m; and arranging the blocks retrieved by the plurality of decision trees in a descending order of the ballot.

In a particular implementation, only the retrieved blocks with ballots greater than a preset threshold value are listed.

In a particular implementation, the step of using a plurality of decision trees to perform block retrieval on the block to be processed comprises: on each decision tree, in response to the block to be processed being judged by the judgment node and reaching the leaf node, acquiring a block belonging to the leaf node as a block retrieval result, wherein the block belonging to the leaf node is set in a manner as follows: training the plurality of decision trees by using a training sample block in a training sample block set so that on each decision tree, the training sample block is judged by the judgment node and reaches a corresponding leaf node, and becomes a block belonging to the corresponding leaf node.

In a particular implementation, a classification tag is preset for the training sample block in the training sample block set so that the retrieved blocks comprised in the block retrieval result also carry classification tags.

According to one embodiment of the present invention, an apparatus for performing block retrieval on a block to be processed of a urine sediment image is provided, comprising: a block retrieval unit configured to use a plurality of decision trees to perform block retrieval on the block to be processed, wherein each of the plurality of decision trees comprises a judgment node and a leaf node, and the judgment node judges the block to be processed to make it reach the leaf node by using a block retrieval feature in a block retrieval feature set to form a block retrieval result at the leaf node, wherein the block retrieval result comprises a retrieved block, and at least two decision trees in the plurality of decision trees are different in structures thereof and/or judgments performed by the judgment nodes thereof by using the block retrieval feature; and an integration unit configured to integrate the block retrieval results of the plurality of decision trees so as to form a final block retrieval result.

In a particular implementation, the integration unit is further configured to: vote for the blocks retrieved by the plurality of decision trees, wherein if there are m decision trees in the plurality of decision trees altogether which retrieve a specific block, the ballot of the specific block is m; and arrange the blocks retrieved by the plurality of decision trees in a descending order of the ballot.

In a particular implementation, the integration unit is further configured to only list the retrieved blocks with ballots greater than a preset threshold value.

In a particular implementation, the block retrieval unit is configured to, on each decision tree, in response to the block to be processed being judged by the judgment node and reaching the leaf node, acquire a block belonging to the leaf node as a block retrieval result, wherein the block belonging to the leaf node is set in a manner as follows: training the plurality of decision trees by using a training sample block in a training sample block set so that on each decision tree, the training sample block is judged by the judgment node and reaches a corresponding leaf node, and becomes a block belonging to the corresponding leaf node.

In a particular implementation, a classification tag is preset for the training sample block in the training sample block set so that the retrieved blocks comprised in the block retrieval result also carry classification tags.

Since in the embodiments of the present invention there is only a need to judge a block to be processed by a judgment node of a decision tree by using a block retrieval feature and there is no need to calculate complex parameters such as a block retrieval feature vector distance, the efficiency of performing block retrieval on a block to be processed of a urine sediment image is improved greatly. Meanwhile, a plurality of decision trees perform block retrieval simultaneously and vote, which improves the precision of block retrieval and makes up for the imprecision influence brought to a final block retrieval result due to the fact that a block retrieval feature used by the judgment of each node on a single decision tree is less complex than parameters such as a block retrieval feature vector distance.

In addition, different from a conventional image retrieval data set, the types of blocks to be processed of a urine sediment image are rare (such as an erythrocyte and a leukocyte), there are lots of block samples of each type and there is a great inter-class difference. This block retrieval resembles classification very much, and thus the block retrieval efficiency may be improved by means of a method of voting via a plurality of decision trees used in classification. In addition, since most of the image retrieval features in an image retrieval feature set used for a urine sediment image are general features, there is no need to compare details, a method of voting by using a plurality of decision trees is more suitable for the image characteristics of a block to be processed of a urine sediment image, which contributes to improving the efficiency and accuracy of block retrieval.

In addition, since in some particular implementations of the present invention, a classification tag is further prepasted to the training sample block in the training sample block set so that the retrieved blocks comprised in the block retrieval result also carry classification tags. In this way, an effect similar to classification is actually achieved. What is better than classification is that it does not provide a classification result but provides several retrieved blocks, each block carries a classification tag, and a user can further judge whether this classification is correct and whether or not to adopt it, which contributes to improving the precision of the classification result.

DESCRIPTION OF THE ACCOMPANYING DRAWINGS

These and other features and advantages of the present invention will become more apparent by way of the detailed description hereinbelow in conjunction with the accompanying drawings.

FIG. 1 shows a flowchart of a method for performing block retrieval on a block to be processed of a urine sediment image according to one embodiment of the present invention.

FIGS. 2a-b show two decision trees according to one embodiment of the present invention.

DETAILED DESCRIPTION OF EMBODIMENTS

Various embodiments of the present invention will be described below in detail in combination with the accompanying drawings.

Figure 1:
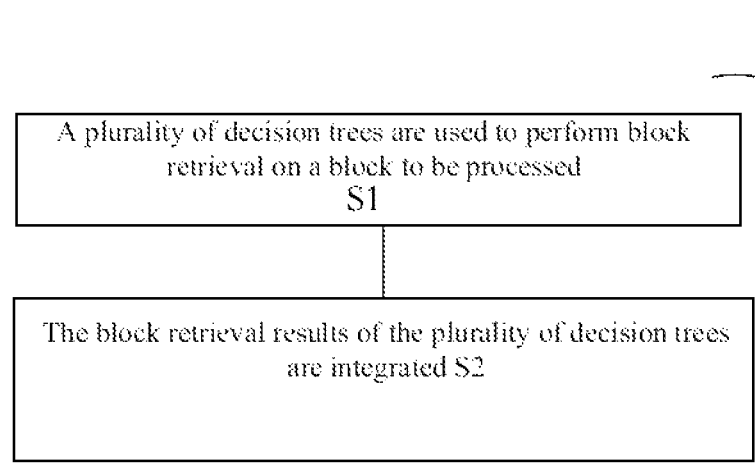

FIG. 1 shows a flowchart of a method 1 for performing block retrieval on a block to be processed of a urine sediment image according to one embodiment of the present invention.

In step S1, a plurality of decision trees are used to perform block retrieval on a block to be processed. Each of the plurality of decision trees comprises a judgment node and a leaf node, and the judgment node judges the block to be processed to make it reach the leaf node by using a block retrieval feature in a block retrieval feature set to form a block retrieval result at the leaf node, and the block retrieval result comprises a retrieved block. At least two decision trees in the plurality of decision trees are different in structures thereof and/or judgments performed by the judgment nodes thereof by using the block retrieval feature.

Figure 2A:
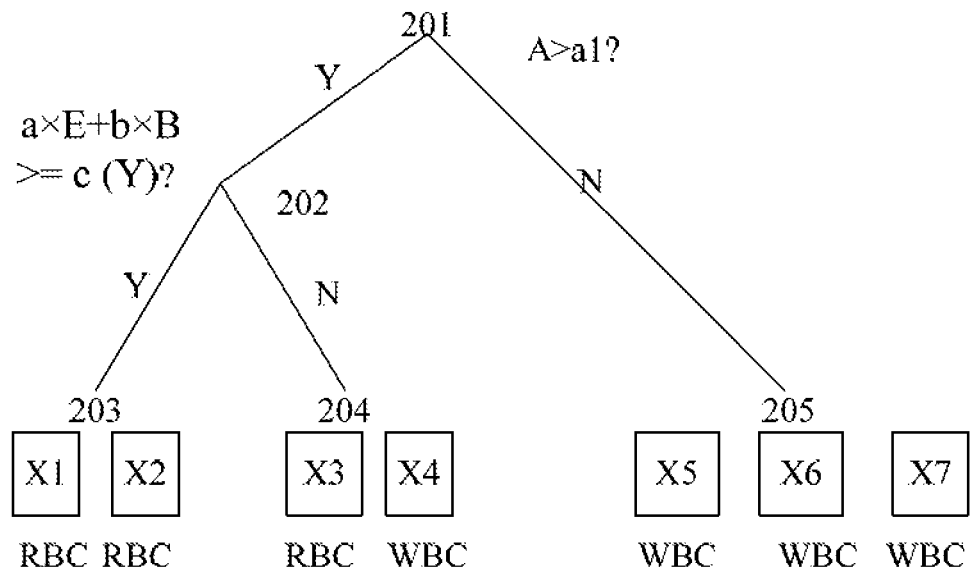
Figure 2B:
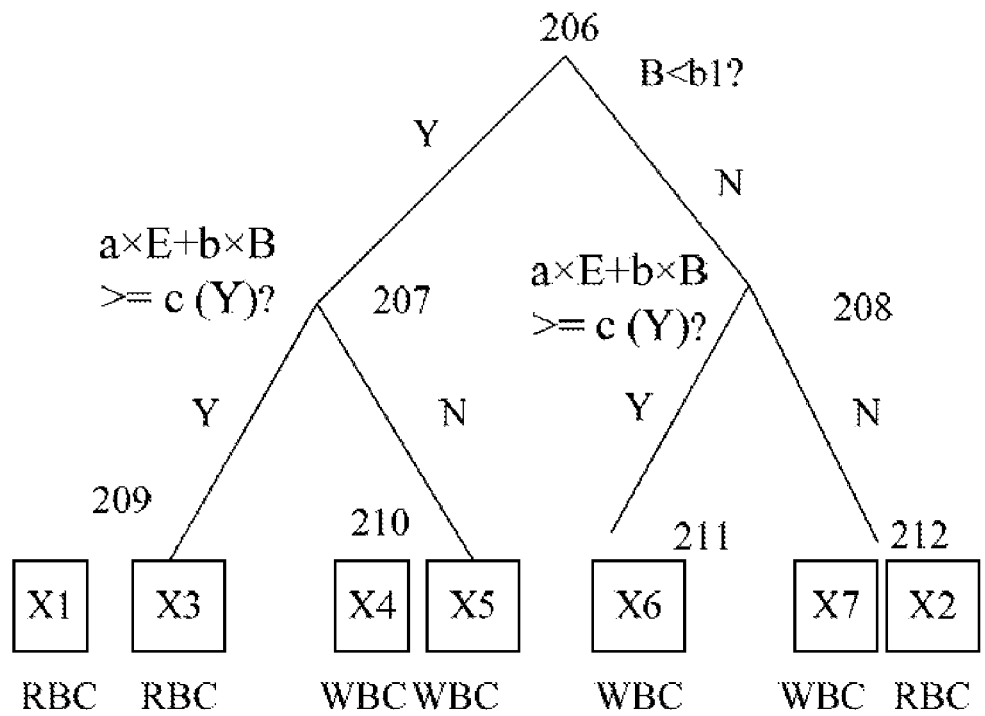

In one embodiment, the judgment of the judgment node is performed by comparing with a preset threshold value. FIG. 2a and FIG. 2b are examples of two decision trees. The decision tree comprises a judgment node and a plurality of leaf nodes. The judgment node comprises a root node and a fork node. In FIG. 2a, the root node comprises a node 201, the fork node comprises a node 202, and the leaf node comprises nodes 203, 204 and 205. In FIG. 2b, the root node comprises a node 206, a fork node comprises nodes 207 and 208, and the leaf node comprises nodes 209-212.

On each decision tree, a training sample block is judged by each judgment node by using a block retrieval feature in a block retrieval feature set and thus reaches a corresponding leaf node, and becomes a block belonging to the corresponding leaf node. It is assumed that there are seven training sample blocks X1-X7 altogether in a training sample block set. There are five block retrieval features A-E in the block retrieval feature set. The block retrieval feature set is similar to a classification feature set, which is known to those skilled in the block retrieval field. On the decision tree of FIG. 2a, at the root node 201, since the feature A of the training sample block X2 is greater than a1, the block reaches the fork node 202. At the fork node 202, the feature of the training sample block X2 is used to judge that $a \times E + b \times B \geq c$ (Y), where a and b are constants concluded in experiments and c (Y) is a threshold value, and therefore the training sample block X2 reaches the leaf node 203 and becomes a block belonging to the leaf node 203. Similarly, on the decision tree of FIG. 2*b*, the training sample block X2 reaches the leaf node 212 and becomes a block belonging to the leaf node 212.

In the training sample block set, classification tags are preset for the training sample blocks X1-X7. For example, it is prejudged that the training sample block X2 is an erythrocyte, and thus a classification tag RBC is pasted to the training sample block X2. Therefore, as shown in FIGS. 2*a-b*, when these training sample blocks reach each leaf node, and after the blocks become blocks belonging to each leaf node, each block has a classification tag.

At least two decision trees in the plurality of decision trees are different in structures and/or judgments performed by the judgment nodes thereof by using the block retrieval feature, because if the plurality of decision trees are completely the same either in the structures or the judgments performed by the judgment nodes by using the block retrieval feature, the trees may become the same decision tree so that there is no sense to vote via a plurality of decision trees subsequently.

On each decision tree, in response to the block to be processed being judged by the judgment node and reaching the leaf node, a block belonging to the leaf node is acquired as a block retrieval result.

For example, with regard to a certain block to be processed X, on the decision tree of FIG. 2*a*, at the root node 201, it is judged that a feature A of the block to be processed X is less than a1, and therefore the block to be processed X reaches the leaf node 205. Blocks X5-X7 belonging to the leaf node 205 are acquired as the block retrieval results of the decision tree of FIG. 2*a*. On the decision tree of FIG. 2*b*, at the root node 206, it is judged that a feature B of the block to be processed X is greater than b1, and therefore the block to be processed X reaches the fork node 208. At the fork node 208, it is judged that the block to be processed X does not meet a×E+b×B>=c (Y), and therefore the block to be processed X reaches the leaf node 212. Blocks X7 and X2 belonging to the leaf node 212 are acquired as the block retrieval results of the decision tree of FIG. 2*b*.

In step S2, the block retrieval results of the plurality of decision trees are integrated so as to form a final block retrieval result.

Firstly, the blocks retrieved by the plurality of decision trees are voted, wherein if there are m decision trees in the plurality of decision trees altogether which retrieve a specific block, the ballot of the specific block is m.

In the example above, the block X7 is retrieved on both of the decision trees of FIG. 2*a* and FIG. 2*b*, and therefore the block X7 obtains two votes. The blocks X5 and X6 are only retrieved on the decision tree of FIG. 2*a*, and therefore each of them obtains one vote. The block X2 is only retrieved on the decision tree of FIG. 2*b*, and therefore also obtains one vote.

Then, the blocks retrieved by the plurality of decision trees are arranged in a descending order of the ballot.

Figure 3:
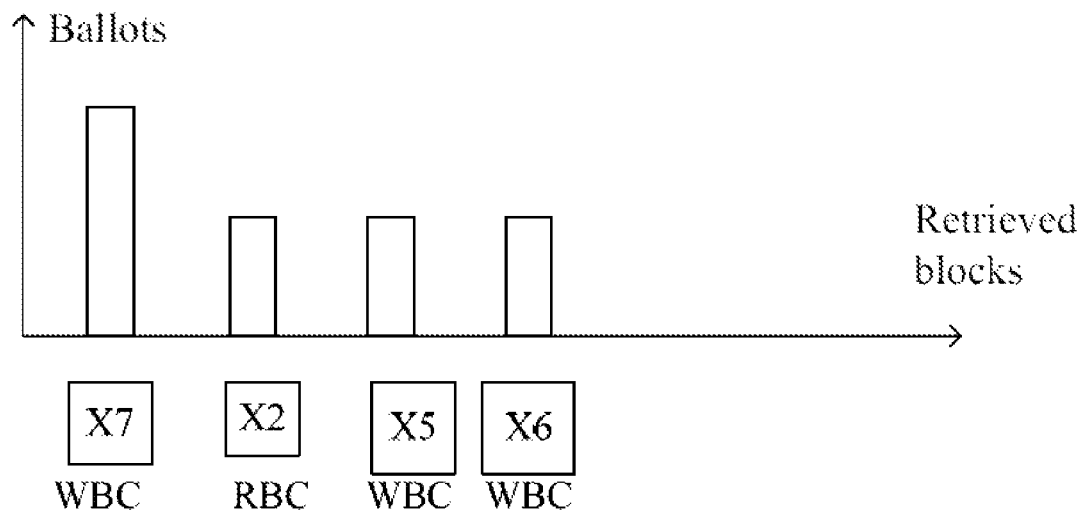
FIG. 3 shows a schematic diagram of presenting the blocks retrieved by the decision trees of FIG. 2a and FIG. 2b in a descending order of ballots according to one embodiment of the present invention.

In the example above, the ballot of the block X7 is the highest, and therefore it is arranged at the front of the retrieved blocks, as shown in FIG. 3.

Other Variants

Those skilled in the art should understand that although a process of performing block retrieval on a block to be processed of a urine sediment image is illustrated in the above-mentioned embodiments by taking two specific decision trees of FIG. 2*a* and FIG. 2*b*, there being seven training sample blocks X1-X7 altogether in a training sample block set, and there being five block retrieval features A-E in the block retrieval feature set as examples, the number of decision trees, the number of training sample blocks in a training sample block set and the number of block retrieval features in a block retrieval feature set may also be other numbers, and the decision trees may also have structures and image retrieval features used by each judgment node which are different from FIG. 2*a* and FIG. 2*b*.

Although in the above-mentioned embodiments, the integration of the block retrieval results of a plurality of decision trees is achieved by voting for the blocks retrieved by the plurality of decision trees and presenting the blocks in a descending order of ballots, voting may also not be performed but the block retrieval results of the plurality of decision trees are listed together. In this way, a user can also find a block retrieval result with a high repetition probability by browsing the block retrieval results of a plurality of decision trees. In addition, only the retrieved blocks with ballots greater than a preset threshold value may also be listed, and these blocks are presented and arranged dispersedly. In addition, only the retrieved blocks with ballots greater than a preset threshold value may also be listed, and these blocks are presented in a descending order of ballots.

Although in the above-mentioned embodiments, blocks belonging to a leaf node on a decision tree are obtained by causing a training sample block in a training sample block set to reach a corresponding leaf node via a judgment node, the method of training may actually not be used and blocks belonging to each leaf node are directly specified, for example, blocks such as an erythrocyte and a leukocyte in a textbook. In this way, the result of performing block retrieval on a block to be processed is not an actual historical sample block but a block in a textbook which is similar to the block to be processed.

Although in the above-mentioned embodiments, a classification tag is preset for a training sample block in a training sample block set so that the retrieved blocks comprised in a block retrieval result also carry classification tags. This approach may help a user to classify the blocks to be processed, but the user may also not perform this processing under the condition where there is no need to know classification information about the blocks to be processed.

In addition, an index of a block belonging to a leaf node of a decision tree may also be only stored in the leaf node, and the block is stored in a database. In response to the block to be processed being judged by a judgment node by using a block retrieval feature in a block retrieval feature set and reaching one leaf node of the plurality of leaf nodes, according to the index stored in the leaf node, a block belonging to the leaf node and corresponding to the index is found in the database. This approach, compared with the approach of directly storing a block belonging to a leaf node in the leaf node, saves the memory space of a processor, thereby acquiring a higher processing speed of the processor.

Figure 4:
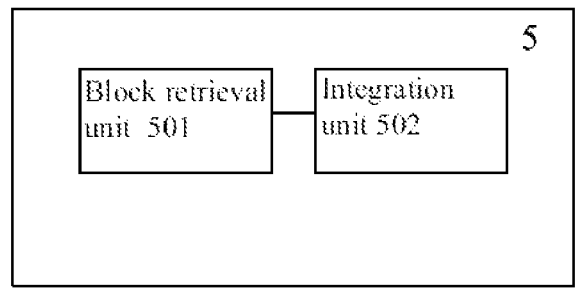
FIG. 4 shows a block diagram of an apparatus for performing block retrieval on a block to be processed of a urine sediment image according to one embodiment of the present invention.

As shown in FIG. 4, an apparatus 5 for performing block retrieval on a block to be processed of a urine sediment image according to one embodiment of the present invention comprises a block retrieval unit 501 and an integration unit 502. The block retrieval unit 501 is configured to use a plurality of decision trees to perform block retrieval on the block to be processed. Each of the plurality of decision trees comprises a judgment node and a leaf node. The judgment node judges the block to be processed to make it reach the leaf node by using a block retrieval feature in a block retrieval feature set to form a block retrieval result at the leaf node. The block retrieval result comprises a retrieved block. At least two decision trees in the plurality of decision trees are different in structures thereof and/or judgments performed by the judgment nodes thereof by using the block retrieval feature. The integration unit 502 is configured to integrate the block retrieval results of the plurality of decision trees so as to form a final block retrieval result. The apparatus 5 can be realized using software, hardware (e.g., an integrated circuit, a FPGA, etc.) or a combination of software and hardware.

In addition, the integration unit 502 may further be configured to: vote for the blocks retrieved by the plurality of decision trees, wherein if there are m decision trees in the plurality of decision trees altogether which retrieve a specific block, the ballot of the specific block is m; and arrange the blocks retrieved by the plurality of decision trees in a descending order of the ballot.

In addition, the integration unit 502 may further be configured to only list the retrieved blocks with ballots greater than a preset threshold value.

In addition, the block retrieval unit 501 may be configured to, on each decision tree, in response to the block to be processed being judged by the judgment node and reaching the leaf node, acquire a block belonging to the leaf node as a block retrieval result, wherein the block belonging to the leaf node is set in a manner as follows: training the plurality of decision trees by using a training sample block in a training sample block set so that on each decision tree, the training sample block is judged by the judgment node and reaches a corresponding leaf node, and becomes a block belonging to the corresponding leaf node.

In addition, a classification tag may be preset for the training sample block in the training sample block set so that the retrieved blocks comprised in the block retrieval result also carry classification tags.

Figure 5:
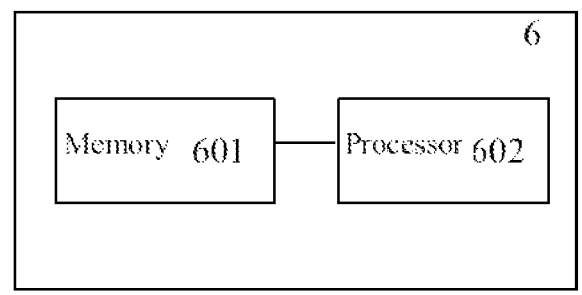
FIG. 5 shows a block diagram of a device for performing block retrieval on a block to be processed of a urine sediment image according to one embodiment of the present invention.

FIG. 5 shows a device 6 for performing block retrieval on a block to be processed of a urine sediment image according to one embodiment of the present invention. The device 6 may comprise a memory 601 and a processor 602. The memory 601 is used for storing an executable instruction. The processor 602 is used for performing an operation performed by each unit in the apparatus 5 according to the executable instruction stored in the memory.

In addition, one embodiment of the present invention further provides a machine-readable medium on which an executable instruction is stored, wherein when the executable instruction is executed, a machine is caused to perform an operation performed by the processor 602.

Those skilled in the art should understand that various variations and modifications can be made to the above various embodiments without departing from the spirit of the present invention. Therefore, the scope of protection of the present invention should be defined by the appended claims.

The invention claimed is:

1. A method for performing block retrieval on a first block to be processed of a urine sediment image, the first block being a portion of the urine sediment image, the method comprising:

using a plurality of decision trees to perform block retrieval on the first block to be processed of the urine sediment image, wherein each of the plurality of decision trees comprises a judgment node and a leaf node, and the judgment node judges the first block to be processed to make it reach the leaf node by using a block retrieval feature in a block retrieval feature set to form a block retrieval result at the leaf node, wherein the block retrieval result comprises one or more retrieved second block, the retrieved second block belonging to the leaf node, and at least two decision trees in the plurality of decision trees are different in structures thereof and/or judgments performed by the judgment nodes thereof by using the block retrieval feature; and integrating the block retrieval results of the plurality of decision trees so as to form a final block retrieval result.

2. The method according to claim 1, characterized in that the step of integrating the block retrieval results of the plurality of decision trees comprises:

voting for the retrieved second blocks by the plurality of decision trees, wherein if there are m decision trees in the plurality of decision trees altogether which retrieve a specific second block, ballot of the specific second block is m, with m being a positive integer; and arranging the retrieved second blocks by the plurality of decision trees in a descending order of the ballot.

3. The method according to claim 2, characterized in that only the retrieved second blocks with ballots greater than a preset threshold value are listed.

4. The method according to claim 1, characterized in that the step of using a plurality of decision trees to perform block retrieval on the first block to be processed of a urine sediment image comprises: on each decision tree, in response to the first block to be processed being judged by the judgment node and reaching the leaf node, acquiring a second block belonging to the leaf node as a block retrieval result, wherein the second block belonging to the leaf node is set in a manner as follows:

training the plurality of decision trees by using a training sample block in a training sample block set so that on each decision tree, the training sample block is judged by the judgment node and reaches a corresponding leaf node, and becomes the second block belonging to the corresponding leaf node.

5. The method according to claim 4, characterized in that a classification tag is preset for the training sample block in the training sample block set so that the retrieved second blocks comprised in the block retrieval result also carry classification tags.

6. A device for performing block retrieval on a first block to be processed of a urine sediment image, comprising:

a memory for storing executable instructions, the executable instructions, when executed, implementing the method of claim 1; and a processor for executing the executable instructions.

7. A non-transitory computer readable medium on which an executable instruction is stored, wherein when the executable instruction is executed, a machine is caused to perform the method of claim 1.

8. An apparatus for performing block retrieval on a first block to be processed of a urine sediment image, comprising:

a block retrieval unit configured to use a plurality of decision trees to perform block retrieval on the first block to be processed of the urine sediment image, wherein each of the plurality of decision trees comprises a judgment node and a leaf node, and the judgment node judges the first block to be processed to make it reach the leaf node by using a block retrieval feature in a block retrieval feature set to form a block retrieval result at the leaf node, wherein the block retrieval result comprises one or more retrieved second block, the retrieved second block belonging to the leaf node, and at least two decision trees in the plurality of decision trees are different in structures thereof and/or judgments performed by the judgment nodes thereof by using the block retrieval feature; and, an integration unit configured to integrate the block retrieval results of the plurality of decision trees so as to form a final block retrieval result;

wherein the block retrieval unit and the integration unit include a processor and a memory storing an executable instruction.

9. The apparatus according to claim 8, characterized in that the integration unit is further configured to:

vote for the retrieved second blocks by the plurality of decision trees, wherein if there are m decision trees in the plurality of decision trees altogether which retrieve a specific second block, ballot of the specific block is m, with m being a positive integer; and arrange the retrieved second blocks by the plurality of decision trees in a descending order of the ballot.

10. The apparatus according to claim 9, characterized in that the integration unit is further configured to only list the retrieved second blocks with ballots greater than a preset threshold value.

11. The apparatus according to claim 8, characterized in that the block retrieval unit is configured to, on each decision tree, in response to the first block to be processed being judged by the judgment node and reaching the leaf node, acquire a second block belonging to the leaf node as a block retrieval result, wherein the second block belonging to the leaf node is set in a manner as follows:

training the plurality of decision trees by using a training sample block in a training sample block set so that on each decision tree, the training sample block is judged by the judgment node and reaches a corresponding leaf node, and becomes a second block belonging to the corresponding leaf node.

12. The apparatus according to claim 11, characterized in that a classification tag is preset for the training sample block in the training sample block set so that the retrieved second blocks comprised in the block retrieval result also carry classification tags.

\* \* \* \* \*